United States Patent [19]
Allain et al.

[11] Patent Number: 5,307,696
[45] Date of Patent: May 3, 1994

[54] LIQUID SAMPLING HEAD HAVING A REMOVABLE NEEDLE BODY IMMERSED IN A CAVITY

[75] Inventors: Jean-Guy Allain; Jean-Louis Kermorgant, both of Equeurdreville; Fernand Rivalain, La Glacerie, all of France

[73] Assignee: Cogema-Compagnie Generale Des Matieres Nucleires, France

[21] Appl. No.: 854,307

[22] Filed: Mar. 19, 1992

[30] Foreign Application Priority Data

Mar. 25, 1991 [FR] France ................................. 9103574

[51] Int. Cl.[5] .................................................. G01N 1/10
[52] U.S. Cl. ........................... 73/864.74; 73/863.810; 73/863.860; 73/864.340; 73/864.520; 141/131
[58] Field of Search .......... 73/863.86, 863.81, 864.74, 73/864.73, 864.52, 864.31, 864.34; 141/130; 604/83, 85, 86; 128/763, 764

[56] References Cited

U.S. PATENT DOCUMENTS

| 4,160,382 | 7/1979 | Finsterwalder et al. | 141/130 |
| 4,512,203 | 9/1985 | Calame-Lonjean et al. | 73/864.31 |

FOREIGN PATENT DOCUMENTS 2058751 5/1971 France .

*Primary Examiner*—Hezrone E. Williams
*Assistant Examiner*—Nashmiya Ashraf
*Attorney, Agent, or Firm*—Pearne, Gordon, McCoy & Granger

[57] ABSTRACT

A head for taking liquid samples and intended to be used in a sampling system associated with a nuclear fuel processing installation, includes a sampling tank (10) in which is removably received a needle body (16), which supports a sampling needle, to which can be fixed a vacuum sampling container (46). The needle body (16) has an extension (34) provided with holes, which surrounds the lower part of the needle (18) immersed in a cavity (26) of the sampling tank (10). The lower end (36) of said extension (34) seals a draining passage (32), which opens into the bottom of the cavity (26). This makes it possible to ensure a larger liquid quantity.

3 Claims, 1 Drawing Sheet

LIQUID SAMPLING HEAD HAVING A REMOVABLE NEEDLE BODY IMMERSED IN A CAVITY

BACKGROUND OF THE INVENTION

The invention relates to a sampling head comprising a needle, whose lower end is immersed in a liquid to be sampled and whose upper end is able to pierce a diaphragm sealing a vacuum sampling container, so that a given quantity of liquid is automatically sampled in said container under the suction effect caused by the vacuum prevailing within the container.

In certain industries, such as the chemical and nuclear industries, it may prove necessary to carry out analyses of liquids present in installations. This more particularly applies to certain radioactive liquids in nuclear fuel processing installations.

In order not to disturb the operation of the installation, punctual sampling takes place of the quantities necessary for these analyses. As described in FR-A-1,401,298 and FR-A-2,058,751, a known solution consists of using for this purpose a liquid sampling system having several sampling heads individually connected to different parts of the installation, so as to make it possible to take samples of different radioactive liquids. The sampling system also has a tool system installed in a glove box, which makes it possible to fix a diaphragm sealing the end of a vacuum container to the needle of one of the sampling heads. The latter are then arranged in circular manner to the bottom of a glove box, so that a tool fitted to a rotary plug arranged coaxially to said circle gives access to each of the sampling heads.

In a sampling system of this type, each sampling head comprises a sampling tank fixed in the bottom of the glove box and a removable needle body supporting the needle, which is fitted into a receptacle of the sampling tank. Below the receptacle the needle is immersed in a cavity formed in the sampling tank and at the upper end of which is open to an intake tube and a discharge tube for a fluid to be sampled. These two tubes connect the sampling head to the installation in which the fluid is to be sampled, so that said fluid circulates in the sampling head at least when a sample has to be made on said head. Moreover, a small cross-section passage connects the bottom of the cavity to one of the tubes, in order to permit the emptying or drainage of the cavity when the circulation of the liquid to be sampled in the sampling head is stopped.

In such a sampling head, the drainage passage issuing into the bottom of the cavity helps to create turbulence within the latter. Thus, instead of only sampling the liquid, it frequently occurs that the containers suck in a large amount of gas, so that the liquid quantity sampled in the container proves inadequate for the analyses to be carried out. However, it is not possible to avoid the existence of the draining passage, because the need to drain the cavity every so often is vital for the quality of the samples taken.

SUMMARY OF THE INVENTION

The present invention specifically relates to a head for taking liquid samples comprising a needle body, whose modified shape makes it possible to permanently ensure the filling of the cavity with liquid and the optimum calming of that part of the liquid in which sampling takes place, without however eliminating the draining passage.

According to the invention, this result is obtained by means of a head for taking liquid samples comprising a sampling tank having a receptacle in which is received a removable needle body carrying a sampling needle, whereof a lower end is immersed in a cavity formed in the sampling tank, below the receptacle, the sampling tank also having a liquid intake tube and a liquid discharge tube which open into the upper end of the cavity and a draining passage connecting the bottom of the cavity to one of the tubes, wherein the needle body has an extension surrounding the needle and whereof a lower end seals the draining passage when said needle body is received in the receptacle, holes being formed in the extension in order to link the cavity with a space defined around the needle within the extension.

In a thus constructed sampling head, the sealing of the draining passage by the end of the extension of the needle body permanently ensures the filling of the cavity with liquid to be sampled. Moreover, in view of the fact that the sampled liquid is located in the space formed between the needle and the extension of the needle body, which is linked with the cavity by holes formed in the extension, the liquid sample in which sampling takes place is perfectly calmed. Therefore, when a container is fixed to the needle, an adequate liquid quantity is sucked into the container by the vacuum initially prevailing there.

In a preferred embodiment of the invention, the lower end of the extension of the needle body has a reduced diameter portion, which normally penetrates an upper end having the same diameter of the draining passage, when the needle body is received in the receptacle.

Moreover, the holes formed in the extension of the needle body advantageously include at least one hole opening substantially into the liquid intake tube and one hole positioned essentially level with the lower end of the needle.

BRIEF DESCRIPTION OF THE DRAWINGS

The invention is described in greater detail hereinafter relative to a non-limitative embodiment and the attached drawings, wherein show.

DETAILED DESCRIPTION OF THE PREFERRED EMBODIMENT

Figure 1:
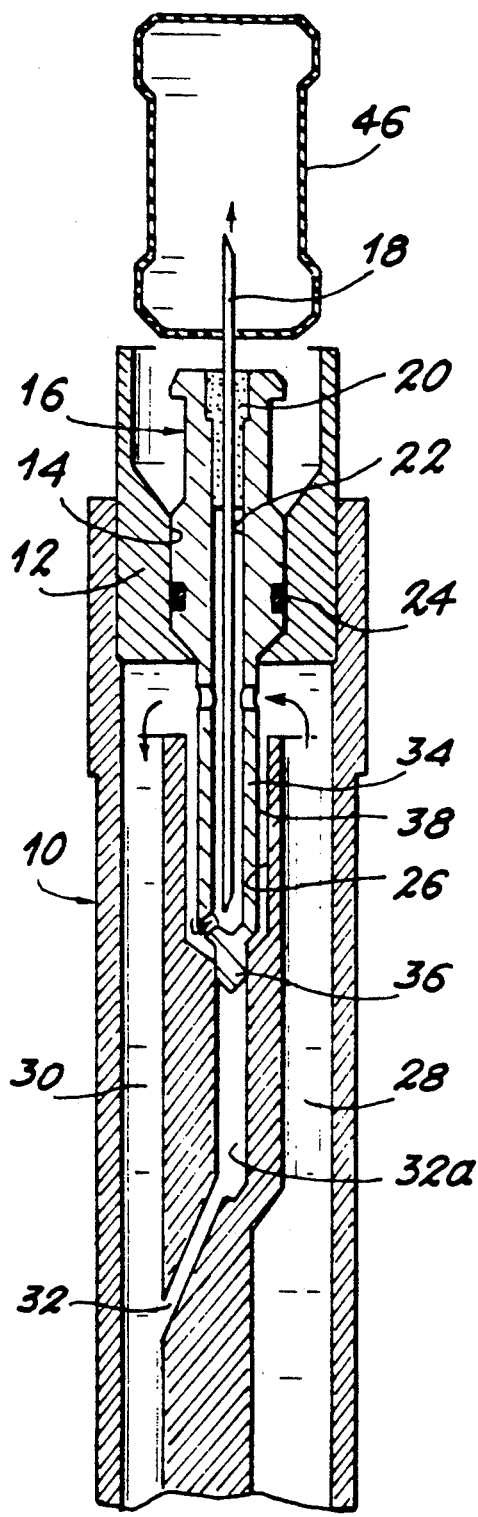
FIG. 1 a longitudinal sectional view diagrammatically showing a liquid sampling head according to the invention.

FIG. 1 shows a head for taking liquid samples for use in a sampling system like that described in FR-A-1,401,298. This sampling head has a sampling tank, designated by the general reference 10 and which is designed for fixing to the bottom of a glove box of the sampling system.

In its upper part, the sampling tank 10 has a sleeve-like element 12 internally defining a receptacle 14. A removable needle body designated by the general reference 16, is force fitted into the receptacle 14, so as to enable it to be replaced when necessary.

The generally tubular needle body 16 internally supports a rectilinear sampling needle 18. More specifically, the fitting of the sampling needle 18 in the needle body 16 is ensured by a tubular crimping member 20 traversed by the needle 18 and which is fitted in the upper stepped portion of a bore 22 formed over most of the height of the needle body 16.

A seal between the element 12 and the needle body 16 is ensured by an annular packing 24 fitted in an annular groove formed in that portion of the needle body 16 received in the receptacle 14.

Below the element 12, the sampling tank 10 forms a cavity 26, arranged in accordance with the axis of the receptacle 14, and at the upper end of which is open to a sampling liquid intake tube 28 and a discharge tube 30 for the said liquid. The intake tube and the discharge tube are connected to a fluid line containing a fluid desired to be tasted, such as a radioactive liquid line in a nuclear processing installation. Moreover, a draining passage 32 connects the bottom of the cavity 26 to the liquid discharge tube 30. The upper end 32a of said passage 32 and which is open into the cavity 26 is positioned coaxially to the latter and has a uniform diameter.

According to the invention and as illustrated in greater detail in FIG. 2, the needle body 16 has, in its portion positioned below the element 12, a tubular extension 34, terminated at its lower end by a reduced diameter cylindrical portion 36. Said cylindrical portion 36 enters the upper end 32a of the draining passage 32 when the needle holder 16 is received in the receptacle 14, as illustrated in the drawings. The external diameter of the cylindrical portion 36 is substantially equal to the diameter of the upper end 32a of the passage 32, so that communication between the cavity 26 and said passage is then interrupted.

As illustrated in FIG. 1, the external diameter of the tubular extension 34 of the needle body 16 is significantly smaller than the internal diameter of the cavity 26, so that a normally liquid-filled annular space 38 is formed in the cavity 26 around the extension 34.

Moreover, the bore 22 formed in the needle body 16 is extended downwards within the extension 34 to the vicinity of the cylindrical portion 36, slightly beyond the lower end of the needle 18, so as to define an annular space 40 around the latter. This annular space 40 is linked with the exterior by holes 42 formed in the extension 34 approximately level with the lower end of the needle 18 and by holes 44 formed in the extension 34 just below the element 12, and opening substantially into the ends of the tubes 28 and 30 which open into the cavity 26.

Figure 2:
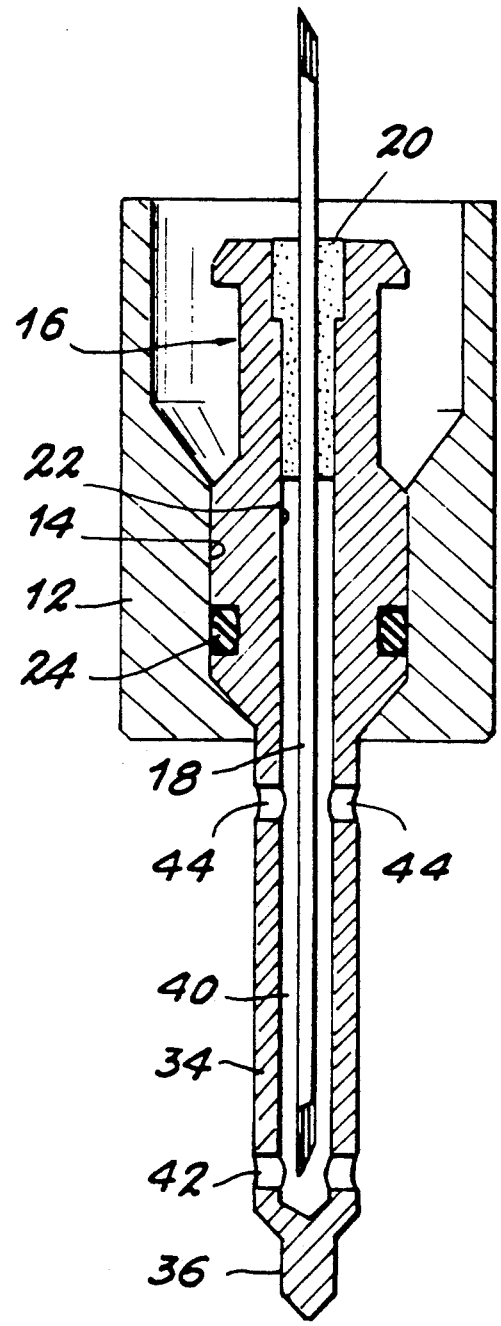
FIG. 2 a longitudinal sectional view illustrating on a larger scale the detachable part of the sampling head of FIG. 1.

In the arrangement described hereinbefore with reference to FIGS. 1 and 2, when the needle body 16 is in place in the receptacle 14, the cylindrical portion 36 seals the upper end 32a of the draining passage 32, so that the annular space 38 formed in the cavity 26 around the extension 34 is permanently filled with liquid. Moreover, in view of the fact that the annular space 40 formed around the needle 18 within the extension 38 permanently communicates with said space 38 by the holes 42 and with the tubes 28, 30 by the holes 44, that portion of the space 40 in which is immersed the needle 18 is also permanently filled with liquid in an undistrubed state. However, a permanent replenishment of said liquid is ensured by the holes 42 and 44, so that a good representative liquid sample is taken.

Thus, these different characteristics make it possible, when the diaphragm of a container 46 is fixed to the upper end of the needle 18 in the manner illustrated in FIG. 1, to sample an adequate liquid quantity to carry out the desired analyses. Moreover, the quality of said analyses is not affected by a possible stagnation of that part of the liquid in which the sample is taken.

The sampling head according to the invention makes it possible to every so often empty the cavity 26 by raising the needle body 16 or by completely removing it with the aid of appropriate tools placed in the glove box overhanging the sampling head, whereby said tools can be constructed in the manner described in FR-A-2,058,751.

Obviously, the invention is not limited to the embodiment described in exemplified manner hereinbefore and covers all variants thereof. Thus, the holes 42 and 44 could be replaced by slots extending through the extension 34 from the lower end of the needle 18 to the vicinity of the element 12, in the area where the tubes 28 and 30 issue.

We claim:

1. A head for taking liquid samples, comprising a sampling tank having a receptacle, a cavity formed below the receptacle, a liquid intake tube and a liquid discharge tube each with openings at an upper end of said cavity, and a draining passage connecting the bottom of the cavity to one of said tubes, the sampling head further comprising a removable needle body carrying a sampling needle, said needle body being adapted to be received in said receptacle with a lower end of said needle body received in said cavity, wherein the needle body has an extension surrounding the needle, means for sealing the draining passage when the needle body is received in the receptacle, and holes formed in the extension in order to link the cavity with a space defined around the needle within the extension.

2. The sampling head according to claim 1, wherein a lower end of the extension has a portion which enters an upper end of said draining passage when the needle body is received in the receptacle, the upper end of said draining passage having a diameter generally equal to that of said portion.

3. The sampling head according to claim 2 or 1, wherein said holes comprise at least one hole opening substantially into the liquid intake tube at the upper end of the cavity, and at least one hole formed substantially level with a lower end of said sampling needle.

* * * * *